US00PP10491P

United States Patent [19]

Sorensen

[11] Patent Number: Plant 10,491

[45] Date of Patent: Jul. 14, 1998

[54] OSTEOSPERMUM PLANT NAMED 'CAPE DAISY NAMAQUA'

[75] Inventor: Carl Aksel Kragh Sorensen, Åbyhoj, Denmark

[73] Assignee: Paul Ecke Ranch, Encinitas, Calif.

[21] Appl. No.: 695,340

[22] Filed: Aug. 9, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 9,897 5/1997 Perry ..... Plt./68.1

*Primary Examiner*—James R. Feyrer
*Assistant Examiner*—Kent L. Bell
*Attorney, Agent, or Firm*—Arnold, White & Durkee

[57] ABSTRACT

A new and distinct cultivar of Osteospermum named 'Cape Daisy Namaqua', particularly characterized by its upright growth habit with unique white, spoon-shaped ray florets, early flowering, medium green foliage, and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Cape Daisy Namaqua', and was developed by the inventor Carl Aksel Kragh Sorensen in Aarhus, Denmark by crossing 'Cape Daisy No. 9332103' with 'Cape Daisy White Fantasy'.

Asexual reproduction by terminal (stem tip) cuttings taken by me or under my supervision in Aarhus, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A white flower color with a unique spoon-shaped petal.
2. An upright compact growth habit.
3. Late season flower response.
4. Well suited for 6" pots, nursery containers, and hanging baskets.

'Cape Daisy Namaqua' is similar to the plant described in co-pending application Ser. No. 08/698,342 cultivar 'Sunny Sonja'. The flower color of 'Cape Daisy Namaqua' is white compared to bright purple for 'Sunny Sonja'.

Chart A compares 'Cape Daisy Namaqua' with 'Sunny Sonja' which is the closest comparable plant to the knowledge of the inventor.

CHART A

| Characteristic | 'Cape Daisy Namaqua' | 'Sunny Sonja' |
|---|---|---|
| Plant Height (above the pot) | 38 cm | 38 cm |
| Plant Width | 52 cm | 67 cm |
| Flower Diameter | 6 cm | 6 cm |
| Color-Mature ray petals | White | Purple |

DESCRIPTION OF PHOTOGRAPH

The accompanying colored photograph is a top perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif. Three rooted cuttings were transplanted into 26 cm (10 inch) having baskets on Jan. 8, 1996. Plants were pinched on Jan. 29, 1996, and received plant growth regulator on February 12 and 26. The values, measurements and observations noted below were taken from plants in bloom on Apr. 12, 1996 and continued to flower through April 1996.

On Apr. 24, 1996, I observed three plants in a 26 cm hanging basket 38 cm tall. This basket had three branched plants with an overall height of 50 cm and an overall width of 52 cm. Each plant had 6 strong branches, originating from within 1.5 cm of the soil line, for a total of 18 branches. Each branch was approximately 36 cm long terminating in a flower. Observation on three plants showed there were 9 flowers open and 85 flower buds in various stages of development. Five to six secondary shoots subtend the terminal flower from the top 5–6 nodes on the primary shoot. These secondary shoots wre approximately 15 cm in length and terminated in a flower.

Color references are made to The Royal Horitcultural Society Colour Chart (R.H.S.), except where general terms of ordinary dictionary significance are used.

THE PLANT

Origin: Seeding from cross pollination.

Parentage: Cross between seed parent '9332103' and pollen parent 'White Fantasy'.

Classification:

*Botanical.—Osteospermum ecklonis.*

*Common name.—Osteospermum.*

*Cultivar name.*—'Cape Daisy Namaqua'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

Plant description:

A. *Form.*—Symmetrical, upright growing perennial shrub, with good branching characteristics after pinching, giving the plant a full appearance.

B. *Habit of growth.*—Vigorous, mounding habit, producing approximately 22 leaves per stem and terminating in flowers. Growth is determinate and flowering on secondary shoots is continuous in cool climates.

C. *Foliage description.*—1. Leaf shape: Obovate with acute tip and attenuate leaf base. 2. Leaf blade size: Mature leaves 11.5 cm long and 4.5–5 cm wide. 3. Petiole length: Approximately 2.5 cm in length. 4. Leaf margin: Slightly sinuate with 3–5 pointed lobes on either side of the leaf blade. 5. Leaf texture: Slightly undulant and twisted at the tip. (i) Upper surface: Slightly pubescent with short, white trichomes evenly distributed throughout the leaf surface. (ii) Under surface: Glabrous. 6. Leaf color: Dark green. (i) Upper surface: Darker than R.H.S. 147B. (ii) Under surface: Near R.H.S. 147B. 7. Venation: Venation is palmately branched with light green colored mid-rib on upper surface. One prominent raised vein is prevalent and two less prominent veins are located on either side of the mid-vein on the under surface. 8. Fragrance: Fragrance is that characteristic of Osteospermum plant species, particularly noted when foliage is wet.

Inflorescence description: Daisy type composite flower with disc florets and ray florets that close at night and open in the morning. One ray floret subtends each pistillate flower part. The disc florets contain male flower parts.

A. *Flowering habits.*—Flowering is determinate with one primary flower at the end of a long, 14 cm pedicel on open flowers. Each pedicel had approximately 3–5 leaflets on the proximal end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates.

C. *Flower buds.*—Flower buds develop successively on secondary branches, reaching a size of 1.8 cm long and 1.3 cm wide prior to opening.

D. *Flowers borne.*—Singularly 5 cm above the plant canopy.

E. *Quantity of flowers.*—Secondary flowers occur progressively around the primary flower so that tight buds to mature flowers are visible at the same time.

F. *Florets.*— 1. Number of petals: 24–25 ray florets and numerous disc florets, making up a flower disk approximately 1.3 cm in diameter. 2. Shape: Narrow linear florets with obtuse to acute tips and acute bases. Ray florets are approximately 2.5 cm long and 0.6 cm wide with a mid-section curling to 0.2 cm wide. 3. Color: Ray florets are white: disc florets are deep violet-blue. (i) Upper surface of ray florets: Pure white, whiter than R.H.S. 155D (ii) Under surface of ray florets: Peripheral edges violet, near R.H.S. 84C and fading to R.H.S. 94D at the petal base; strip along mid-rib is grey/orange, near R.H.S. 174C. (iii) Disc florets: Near R.H.S. 89A. 4. Surface: (i) Upper surface of ray florets: Glabrous. (ii) Under surface of ray florts: Glabrous but pubescent near the base. 5. Inflorescence: Up to 6 cm in diameter. 6. Fragrance: None.

G. *Reproductive organs.*— 1. Stamens: Short stamens emerge on outermost disc florets and progress toward the center. 2. Anther: Each disc floret has 1 stamen terminating in a 5-part anther. 3. Pollen: Copious and golden yellow. 4. Stigma: Bipartite 5. Styles: Short, approximately 2 mm long and purple. 6. Ovary: Inferior to both disc and ray florets and green in color. 7. Ray florets contain pistillate flower parts and disc florets contain staminate and flowr parts.

What is claimed is:

1. A new and distinct cultivar of Osteospermum plant named 'Cape Daisy Namaqua', as illustrated and described.

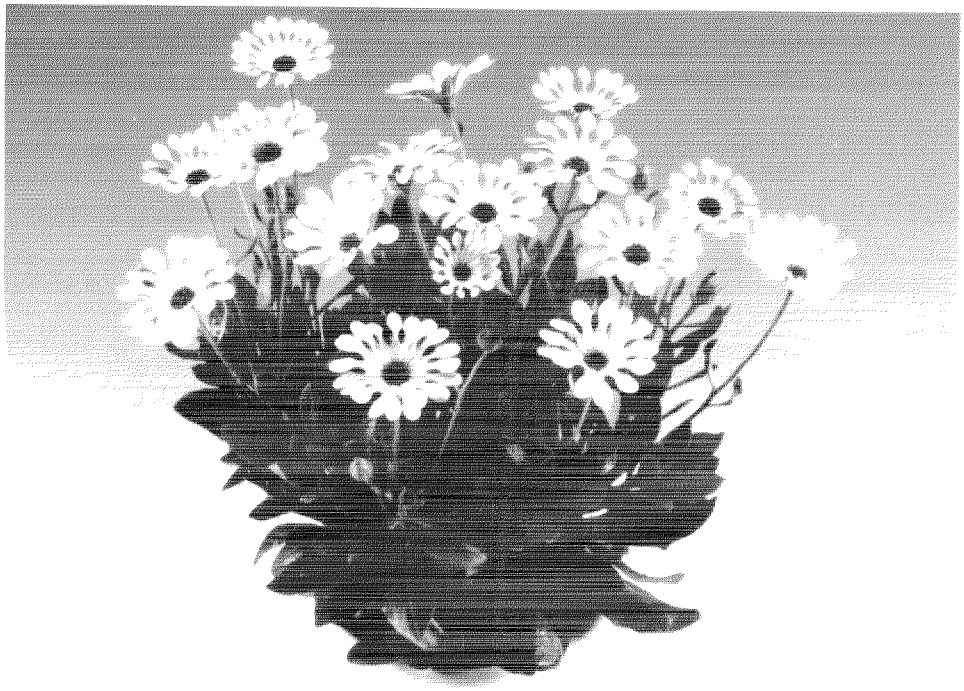

* * * * *